US00PP11368P

United States Patent [19]

Dümmen

[11] Patent Number: Plant 11,368

[45] Date of Patent: May 2, 2000

[54] POINSETTIA PLANT NAMED 'DUENIA'

[75] Inventor: Marga Dümmen, Rheinberg, Germany

[73] Assignee: Dummen Jungpflanzenkulteren, Rheinberg, Germany

[21] Appl. No.: 09/038,769

[22] Filed: Mar. 11, 1998

[51] Int. Cl.[7] ..... A01H 5/00

[52] U.S. Cl. ..... Plt./307

[58] Field of Search ..... Plt./307

[56] References Cited

U.S. PATENT DOCUMENTS

| | | | |
|---|---|---|---|
| P.P. 7,338 | 9/1990 | Hrebeniuk | Plt./307 |
| P.P. 7,825 | 3/1992 | Fruehwirth | Plt./307 |
| P.P. 7,883 | 6/1992 | Fruehwirth | Plt./307 |
| P.P. 10,162 | 12/1997 | Gross | Plt./307 |
| P.P. 10,763 | 1/1999 | Didden | Plt./307 |

*Primary Examiner*—Howard J. Locker
*Assistant Examiner*—Kent L. Bell
*Attorney, Agent, or Firm*—C. A. Whealy

[57] ABSTRACT

A new and distinct variety of Poinsettia plant named 'Duenia', characterized by its bright red flower bracts that are oak-leaf shaped and angled upright with respect to stem axis; freely branching plant habit; and excellent postproduction longevity.

1 Drawing Sheet

BACKGROUND OF THE INVENTION

The present invention relates to a new and distinct variety of Poinsettia plant, botanically known as *Euphorbia pulcherrima* Willd., and hereinafter referred to by the name 'Duenia'. The new variety is a product of a mutation induction breeding program conducted by the inventor in Rheinberg, Germany. The objective of the breeding program is to create new Poinsettia cultivars having desirable bract and foliage color and form and good post-production longevity. The new cultivar originated by exposing cuttings of the commercial Poinsettia variety 'Fisson' (disclosed in U.S. Plant Pat. No. 9,365) to an x-ray radiation level to 25 to 30 rads in 1996. Following the radiation treatment, the cuttings were rooted and cuttings were harvested, planted and flowered in a controlled environment in Rheinberg, Germany. The variety 'Duenia' was discovered and selected by the inventor as a single flowering plant within this population. The selection of this plant was based on its desirable bract color, leaf shape, bract orientation and good post-production longevity. Asexual reproduction of the new variety by terminal cuttings taken at Rheinberg, Germany, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duenia'. These characteristics in combination distinguish 'Duenia' as a new and distinct variety:

1. Bright red flower bracts.
2. Oak-leaf shaped flower bracts.
3. Flower bracts angled upright with respect to stem axis.
4. Freely branching plant habit.
5. Excellent postproduction longevity.

In side-by-side comparisons conducted by the inventor in Rheinberg, Germany, plants of the new Poinsettia differed from plants of 'Fisson' in the following characteristics:

1. Flower bracts of plants of the new variety are brighter red than flower bracts of plants of 'Fisson'.

2. Flower bracts of plants of the new variety are orientated more upright than flower bracts of plants of 'Fisson'.

3. Leaves of plants of the new variety are shorter and broader than leaves of plants of 'Fisson'.

BRIEF DESCRIPTION OF THE PHOTOGRAPH

The accompanying colored photograph illustrates the overall appearance of the new variety, showing the colors as true as it is reasonably possible to obtain in a colored reproduction of this type. The photograph comprises a top perspective view of a typical plant of 'Duenia' that was pinched and grown in a 15-cm container.

DETAILED BOTANICAL DESCRIPTION

The variety 'Duenia' has not been observed under all possible environmental conditions. The phenotype may vary somewhat with variations in environment such as temperature, daylength and light intensity, without, however, any variance in genotype. The following observations and measurements describe plants grown in Rheinberg, Germany, under commercial practice in a glass-covered greenhouse with day temperatures about 22° C., night temperatures about 18° C. and light levels about 30,000 to 40,000 lux. Plants were grown in 15-cm pots, pinched one time, and flowered under long nyctoperiods. In the following description, color references ae made to The Royal Horticultural Society Colour Chart except where general terms of ordinary dictionary significance are used.

Botanical classification: *Euphorbia pulcherrima* Willd. 'Duenia'.

Parentage: Induced mutation of *Euphorbia pulcherrima* Willd. 'Fisson'.

Propagation:

*Type cutting.*—Terminal cuttings.

*Time to develop roots.*—Summer: About 18 days at 28° C. Winter: About 24 days at 20° C.

*Rooting habit.*—Fine, freely branching.

Plant description:

*Plant form.*—Inverted triangle, top of plant rounded.

*Growth habit.*—Freely branching and upright. Branching is enhanced by removing the shoot apex. Moderate growth rate, but vigorous. Suitable for 6 to 16-cm containers.

*Plant height.*—About 23 cm.

*Crop time.*—From unrooted cuttings to a flowering plant in a 15-cm container, about 15 weeks are required.

*Foliage description.*—Quantity of leaves: Usually 65 to 75 per flowering plant. Length: About 12 cm. Width: About 9.5 cm. Shape: Deltoid, deeply lobed, star-shaped. Apex: Apiculate. Base: Acute. Texture: Velvety, glabrous. Color: Young foliage, upper surface: 147A. Young foliage, lower surface: 139B. Mature foliage, upper surface: 147A. Mature foliage, lower surface: 139B. Venation, upper surface: Light green. Venation, lower surface: Light green. Petiole: Length: About 3 cm. Color: Upper surface, 131A; lower surface: 139A.

Inflorescence description:

*Inlflorescence type and habit.*—Inflorescences are compounds corymbs of cyathia with colored flower bracts subtending the cyathia.

*Natural flowering season.*—Autumn/winter in Northern Hemishpere. Flower initiation and development can be induced under long nyctoperiod conditions.

*Time to flower.*—About 9 weeks under long nyctoperiod conditions.

*Quantity of inflorescences.*—One per lateral branch, usually about 8 per plant.

*Inflorescence size.*—Diameter: About 40 cm. Height (depth): About 7 cm.

*Flower bracts.*—Orientation: Angled upright about 130 to 145° with respect to stem axis. Quantity of flower bracts per inflorescence: Usually at least 7 fully colored bracts per inflorescence. Length: About 12 cm. Width: About 7.7 cm. Shape: Deeply lobed, oak leaf-shaped. Apex: Apiculate. Texture: Smooth, satiny. Color: Mature, upper surface: 45A, bract color does not fade. Mature, lower surface; 46A.

*Cyathia.*—Quantity: Usually about 8 to 12 per corymb. Diameter of cyathia cluster: About 2.2 cm. Length: About 1.2 cm. Width: About 5.5 mm. Color: Immature: 144A. Mature: 144C. Peduncle: Length: About 1.75 cm. Aspect: Erect. Color: 178A. Stamens: Stamen number: Usually 8 to 10 per cyathium. Anther size: About 1 to 2 mm. Anther shape: Rounded. Pollen color: 8B. Pistils: Pistil number: 1 per cyathium. Stigma shape: Trilobate. Style length: About 1 to 2 mm. Ovary number: Three. Nectaries: Usually one and sometimes two per cyathium.

Disease resistance: No fugal, bacterial nor viral problems observed on plants grown under commercial conditions.

Postproduction longevity: Generally plants maintain good substance and bract color for about five to six weeks under interior conditions.

We claim:

1. A new and distinct variety of Poinsettia plant named 'Duenia', as illustrated and described.

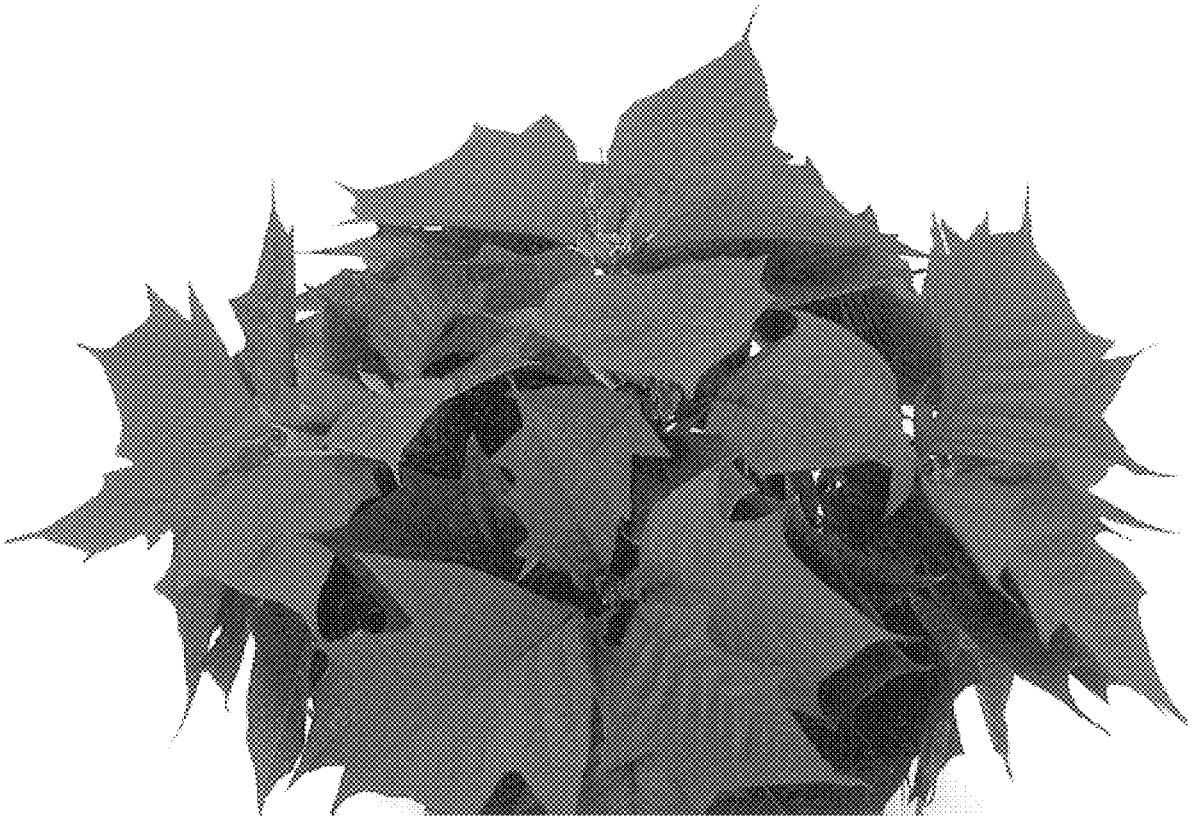

* * * * *